US011125670B2

(12) United States Patent
Kubo et al.

(10) Patent No.: US 11,125,670 B2
(45) Date of Patent: Sep. 21, 2021

(54) DEVICE, SYSTEM AND KIT FOR MEASURING TENSION OF SHEET-LIKE TISSUE CONTAINING CARDIOMYOCYTES

(71) Applicants: NIHON KOHDEN CORPORATION, Tokyo (JP); TOKYO WOMEN'S MEDICAL UNIVERSITY, Tokyo (JP)

(72) Inventors: Hirotsugu Kubo, Tokorozawa (JP); Takahiro Shioyama, Tokorozawa (JP); Yuki Kagawa, Tokorozawa (JP); Tatsuya Shimizu, Tokyo (JP); Daisuke Sasaki, Tokyo (JP)

(73) Assignees: NIHON KOHDEN CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 304 days.

(21) Appl. No.: 16/169,119

(22) Filed: Oct. 24, 2018

(65) Prior Publication Data
US 2019/0120742 A1 Apr. 25, 2019

(30) Foreign Application Priority Data

Oct. 25, 2017 (JP) .............................. JP2017-206587

(51) Int. Cl.
*G01N 13/02* (2006.01)
*A61B 5/00* (2006.01)
(Continued)

(52) U.S. Cl.
CPC ........... *G01N 13/02* (2013.01); *A61B 5/4519* (2013.01); *C12N 5/0657* (2013.01);
(Continued)

(58) Field of Classification Search
CPC ............. G01N 13/02; G01N 33/54366; G01N 2013/0283; A61B 5/4519; C12N 5/0657; C12N 2533/56; B01L 9/52
(Continued)

(56) References Cited

U.S. PATENT DOCUMENTS 3,998,217 A * 12/1976 Trumbull ........... A61B 17/0293
600/233
5,234,559 A * 8/1993 Collier ............. G01N 27/44717
204/464
(Continued)

FOREIGN PATENT DOCUMENTS

CN 103756898 A * 12/2012 ............. C12M 41/24
JP 2-211865 A 8/1990
(Continued)

OTHER PUBLICATIONS

Translation CN-103756898-A (Year: 2014).*
(Continued)

*Primary Examiner* — Herbert K Roberts
*Assistant Examiner* — Monica S Young
(74) *Attorney, Agent, or Firm* — Sughrue Mion, PLLC

(57) ABSTRACT

A device for measuring a tension of a sheet-like tissue containing cardiomyocytes includes a first gel adapter holder having a frame member and a first gel holding member protruding toward a part of an inside face of the frame member for fixing one end of a film-like gel; and a second gel adapter holder having a second gel holding member for fixing the other end of the gel and a connection member connected to the second gel holding member. A kit includes the tension measuring device; a substrate having a pair of gel molding protruding members fitted along the inside face of the frame member; and a gel forming lid body having a face parallel to a gel contact face of the substrate so as to form
(Continued)

an upper face of the gel. Further, a system for measuring the tension includes the tension measuring device.

13 Claims, 11 Drawing Sheets

(51) Int. Cl.
*C12N 5/077* (2010.01)
*G01N 33/543* (2006.01)
*B01L 9/00* (2006.01)

(52) U.S. Cl.
CPC .......... *G01N 33/54366* (2013.01); *B01L 9/52* (2013.01); *C12N 2533/56* (2013.01); *G01N 2013/0283* (2013.01)

(58) Field of Classification Search
USPC .............................................. 73/64
See application file for complete search history.

(56) References Cited

U.S. PATENT DOCUMENTS

| | | | |
|---|---|---|---|
| 5,284,766 A | | 2/1994 | Okano et al. |
| 6,030,340 A | * | 2/2000 | Maffei ............... A61B 17/0206 600/228 |
| 6,057,150 A | * | 5/2000 | Lee ........................ C12M 23/48 435/288.3 |
| 6,107,081 A | * | 8/2000 | Feeback ............... A61B 5/1108 435/284.1 |
| 2013/0171213 A1 | | 7/2013 | Sekine et al. |
| 2013/0173018 A1 | | 7/2013 | Sakaguchi et al. |
| 2014/0094388 A1 | * | 4/2014 | Wakatsuki ........... C12N 5/0697 506/9 |
| 2014/0113365 A1 | * | 4/2014 | Nagai .................... C12M 23/04 435/305.1 |
| 2017/0016885 A1 | * | 1/2017 | Chen-Izu ............... C12M 29/10 |
| 2017/0038335 A1 | * | 2/2017 | Hirabayashi ..... G01N 27/44739 |

FOREIGN PATENT DOCUMENTS

| | | |
|---|---|---|
| WO | 2012/036224 A1 | 3/2012 |
| WO | 2012/036225 A1 | 3/2012 |
| WO | 2015/134589 A1 | 9/2015 |

OTHER PUBLICATIONS

Michael R. Zile et al., "Gel stretch method: a new method to measure constitutive properties of cardiac muscle cells", AJP—Heart and Circulatory Physiology, Jun. 1, 1998, pp. H2188-H2202, XP55545731. (15 pages total).

Zhonggang Feng et al., "An Electro-Tensile Bioreactor for 3-D Culturing of Cardiomyocytes", IEEE Engineering in Medicine and Biology Magazine, IEEE Service Center, Pisacataway, NJ, US, Jul. 1, 2005, pp. 73-79, XP002682110. (7 pages total).

Daisuke Sasaki et al., "Contracrile force measurement of human induced pluripotent stem cell-derived cardiac cell sheet-tissue", PLOS One, vol. 13, No. 5, May 23, 2018, p. 1-21, XP055545535. (21 pages total).

Search Report dated Jan. 30, 2019 by the European Patent Office in counterpart European Patent Application No. 18201938.0.

Yuji Haraguchi et al., "Scaffold-free tissue engineering using cell sheet technology", RSC Advances, vol. 2, The Royal Society of Chemistry, Jan. 4, 2012, pp. 2184-2190.

\* cited by examiner

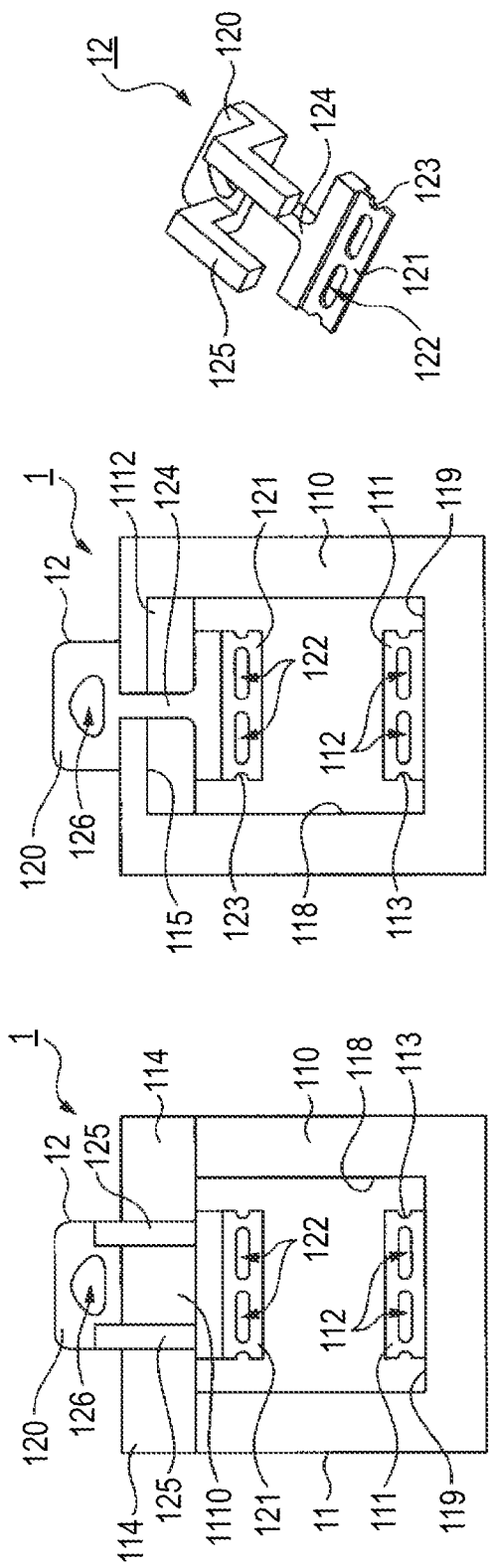

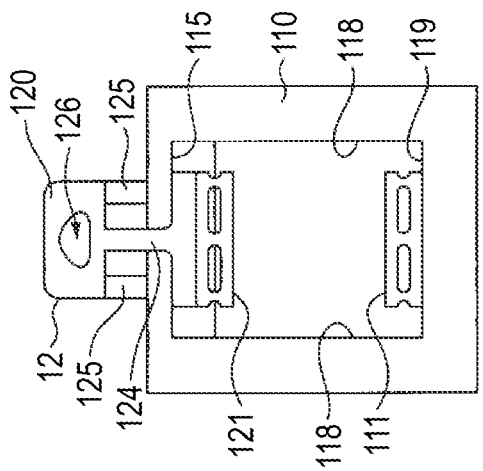
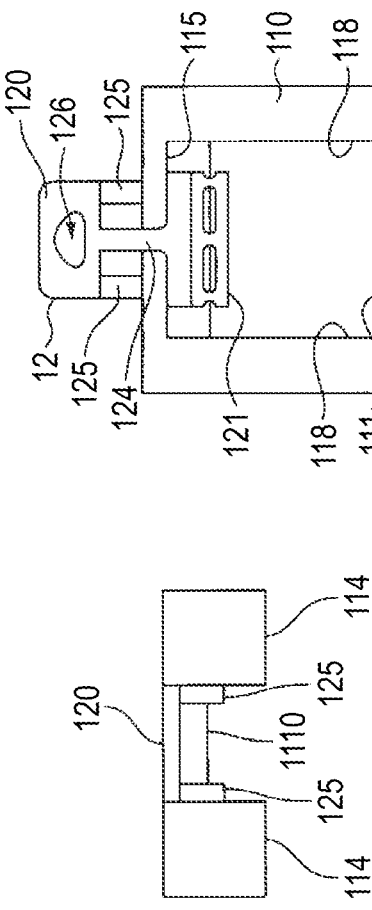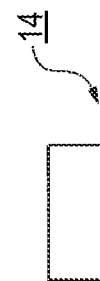
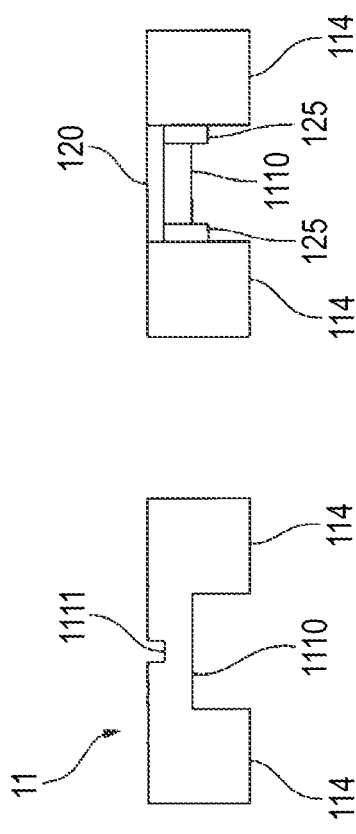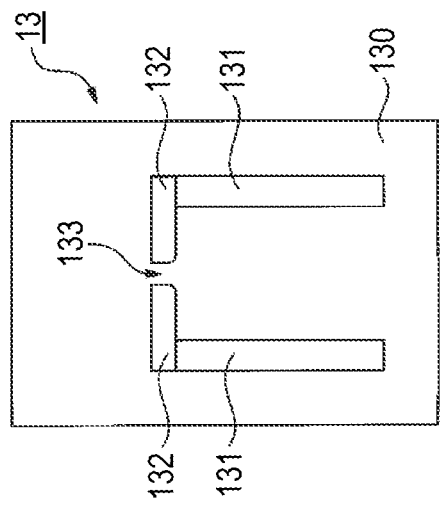

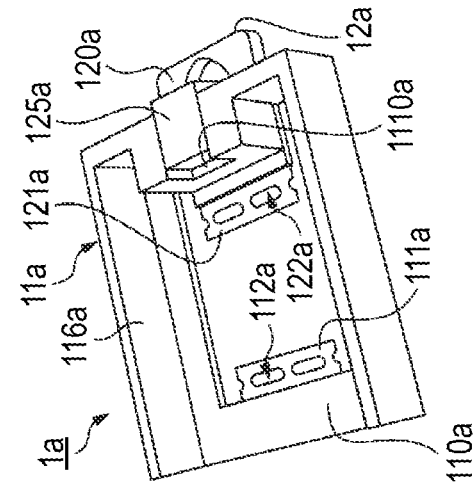
FIG. 3A
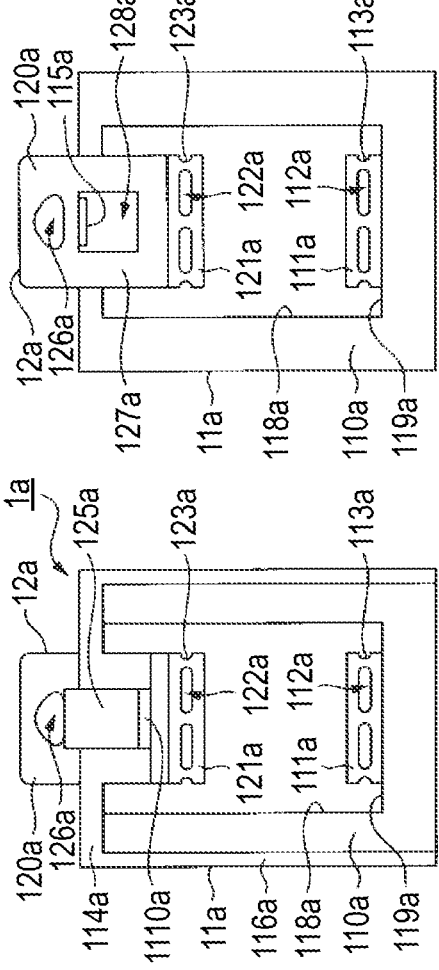
FIG. 3B
FIG. 3C
FIG. 3D FIG. 3E
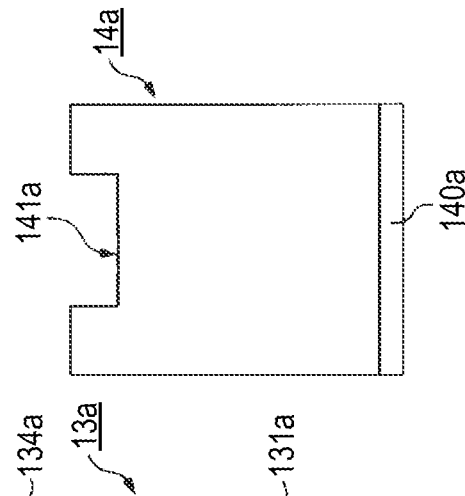
FIG. 3F
FIG. 3G
FIG. 3H
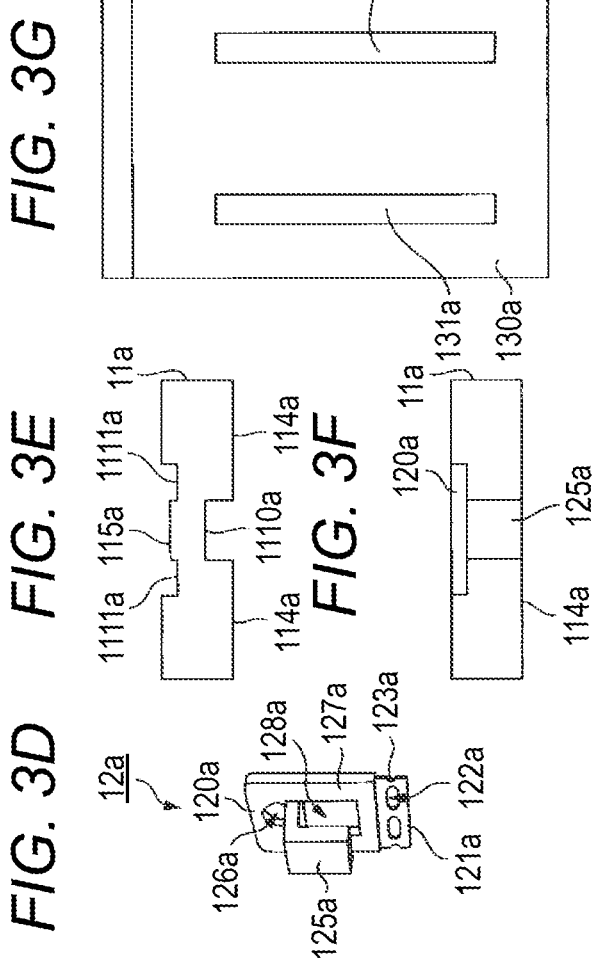

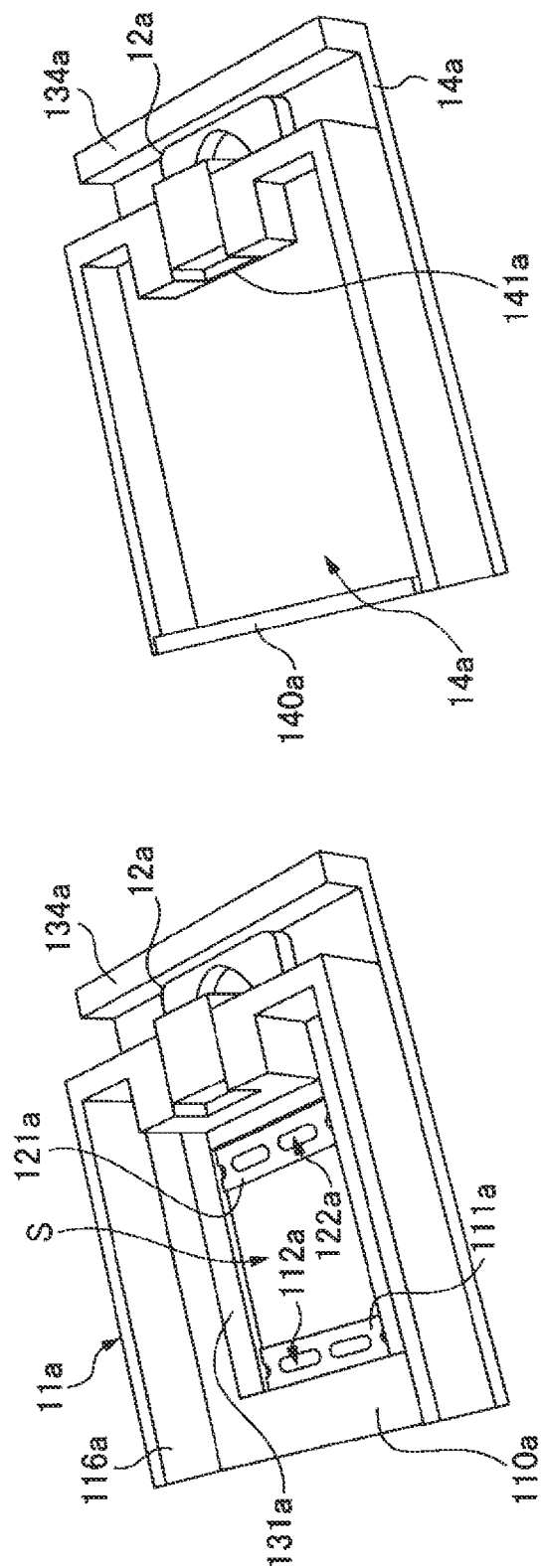

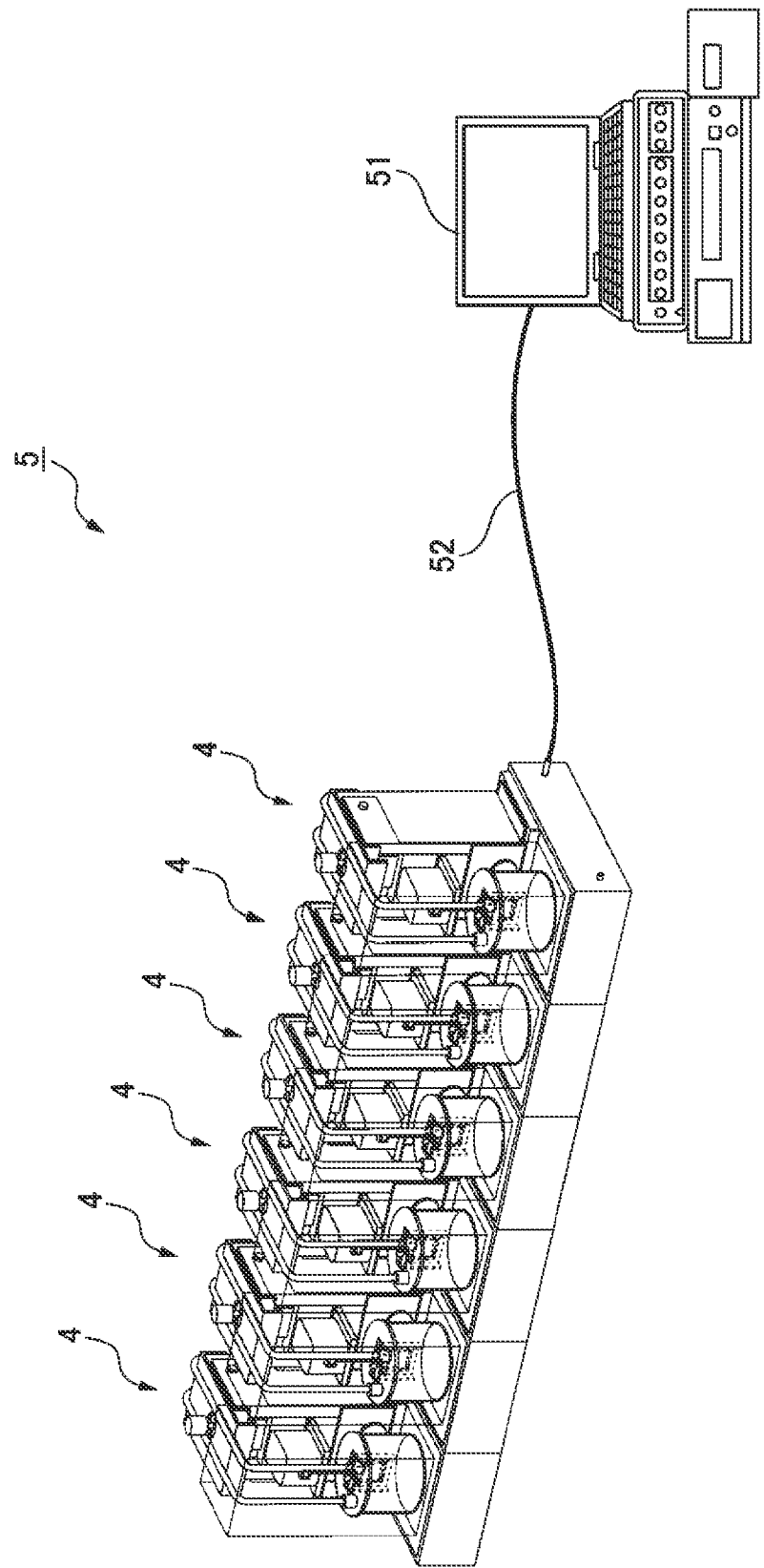

DEVICE, SYSTEM AND KIT FOR MEASURING TENSION OF SHEET-LIKE TISSUE CONTAINING CARDIOMYOCYTES

CROSS-REFERENCES TO RELATED APPLICATIONS

The disclosure of Japanese Patent Application No. 2017-206587 filed on Oct. 25, 2017, including specification, drawings and claims is incorporated herein by reference in its entirety.

TECHNICAL FIELD

The presently disclosed subject matter relates to a device, a system and a kit for measuring the tension of a sheet-like tissue containing cardiomyocytes.

BACKGROUND ART

In drug discovery research, an in vitro study using cultured cells and an in vivo study using experimental animals for evaluating the safety and effectiveness of a developed drug are carried out. In the former study, an in vitro culture system for animal cells is used. In the latter study, evaluation is carried out by a system using experimental animals centered on rodent animals.

In general, it is also said that the success rate of drug discovery is about 1/6000, and because of failure of development of many candidate drugs, the research and development cost for a pharmaceutical company or the like tends to increase. In general, it is also said that an investment of several tens of billion yen is required for developing one type of new drug. The main factor for the failure of new drug development is said to be derived from (1) a difference between an evaluation screening system using cells alone and an actual human biological tissue and (2) a difference between an experimental animal and a human. It has been demanded in the drug discovery and development field that these differences be eliminated to improve the success rate of drug discovery and reduce the research and development cost.

In recent years, a drug discovery screening method utilizing pluripotent stem cells such as iPS cells having an ability to differentiate into various functional cells has been developed. However, a conventionally used evaluation system uses cells alone, and does not reflect the state of a biological tissue. Therefore, it has been demanded that an evaluation system which mimics a biological tissue be developed from somatic cells differentiated and induced from pluripotent stein cells.

As an attempt to three-dimensionally construct cells, for example, a method in which cells are seeded in a three-dimensional structure called "scaffold", a method in which an organ or a tissue is decellularized, and cells are seeded in the remaining matrix to be formed into a three-dimensional shape, a method in which sheets of cells exfoliated in sheets are three-dimensionally stacked, etc. have been developed (for example, Patent Document 1).

As one of the methods for forming a cell sheet, there is a method using a cell culture dish (temperature responsive culture dish) coated with poly(N-isopropylacrylamide) (PIPAAm) (Patent Document 1). An arbitrary cell is cultured on a temperature responsive culture dish coated with PIPAAm, and after the cells become confluent, the temperature is decreased to 20° C. which is lower than 32° C. as the lower critical solution temperature (LCST) of PIPAAm, whereby cells in the form of a sheet (a cell sheet) are obtained noninvasively.

By making full use of such a technique, research and development of an evaluation system to be utilized in drug discovery screening have been performed. As one of the evaluation systems, a myocardial tissue for evaluating the cardiotoxicity of a candidate drug has been tried to be constructed (for example, Patent Documents 2 and 3). However, the construction of the evaluation system by such a method is very complicated, and is not suitable for mass production. Further, muscle contraction cannot be quantitatively measured.

The development of a new evaluation system which can be utilized in a drug discovery screening system, particularly, a cardiotoxicity screening test and also can be mass-produced, and employs a simple procedure has been awaited.

PRIOR ART DOCUMENTS

Patent Documents

Patent Document 1: JP-A-02-211865
Patent Document 2: WO 2012/036224
Patent Document 3: WO 2012/036225

Non-Patent Document

Non-Patent Document 1: Haraguchi Y., et al., Scaffold-free tissue engineering using cell sheet technology, RSC Adv., 2012; 2: 2184-2190

SUMMARY OF THE INVENTION

An object of the presently disclosed subject matter is to provide a device for measuring the tension of a sheet-like tissue containing cardiomyocytes, which enables quantitative measurement of muscle contraction and can be mass-produced, a system, and a kit.

The present inventors carried out research and development in addition to investigation from various angles for achieving the above object. As a result, they arrived at the presently disclosed subject matter providing a device for measuring the tension of a sheet-like tissue containing cardiomyocytes, which enables quantitative measurement of muscle contraction and can be mass-produced, by contriving the form of the device for measuring the tension of a sheet-like tissue containing cardiomyocytes, a system, and a kit. That is, the presently disclosed subject matter is as follows.

[1] A device which is a device for measuring the tension of a sheet-like tissue containing cardiomyocytes, including:
a first gel adapter holder having a frame member and a first gel holding member protruding toward a part of an inside face of the frame member so as to fix one end of a film-like gel; and
a second gel adapter holder having a second gel holding member for fixing the other end of the gel and a connection member connected to the second gel holding member,
wherein the second gel adapter holder is attached to the first gel adapter holder so that the second gel holding member is opposed to the first gel holding member inside the frame member, and
the second gel adapter holder has a mechanism for sliding in an axial direction in which the first gel holding member and the second gel holding member are opposed to each other.

[2] The device according to [1], wherein the first gel holding member has one or more first gel holding openings and the second gel holding member has one or more second gel holding openings.

[3] The device according to [2], wherein two to five first gel holding openings and two to five second gel holding openings are provided.

[4] The device according to any one of [1] to [3], wherein the thicknesses of the first gel holding member and the second gel holding member are thinner than the thickness of the frame member.

[5] The device according to any one of [1] to [4], wherein the thickness of the frame member is from 0.5 mm to 3.0 mm.

[6] The device according to any one of [1] to [5], wherein the first gel adapter holder is provided with a stopper for restricting the slidable range of the second gel adapter holder.

[7] The device according to any one of [1] to [6], wherein a film-like gel is provided between the first gel holding member and the second gel holding member.

[8] The device according to [7], wherein the gel is a hydrogel.

[9] The device according to [7] or [8], wherein the gel is a fibrin gel.

[10] The device according to any one of [7] to [9], wherein a sheet-like tissue containing cardiomyocytes adhered to the film-like gel is provided.

[11] The device according to [10], wherein the sheet-like tissue is a cell sheet.

[12] A system for measuring the tension of a sheet-like tissue containing cardiomyocytes, including:
the device according to [10] or [11],
a culture medium tank for dipping the device;
a tension detection unit which is connected to the connection member of the second gel adapter holder;
an arithmetic unit which is connected to the tension detection unit, arithmetically processes a signal detected by the tension detection unit, and calculates the tension; and
an output unit which displays the result calculated by the arithmetic unit.

[13] The system according to [12], wherein the tension detection unit is a load cell.

[14] A kit for forming the device according to any one of [1] to [9], including:
a first gel adapter holder having a frame member and a first gel holding member provided protruding toward a part of an inside face of the frame member for fixing one end of a film-like gel;
a second gel adapter holder having a second gel holding member for fixing the other end of the gel and a connection member connected to or integrated with the second gel holding member;
a substrate having a pair of gel molding protruding members fitted along the inside face of the frame member; and
a gel forming lid body having a face parallel to a gel contact face of the substrate for forming the upper face of the gel,
wherein the second gel adapter holder is attached to the first gel adapter holder so that the second gel holding member is opposed to the first gel holding member inside the frame member, and
the second gel adapter holder has a mechanism for sliding in an axial direction in which the first gel holding member and the second gel holding member are opposed to each other.

[15] The kit according to [14], wherein the first gel holding member has one or more first gel holding openings and the second gel holding member has one or more second gel holding openings.

[16] The kit according to [14] or [15], wherein the thicknesses of the first gel holding member and the second gel holding member are thinner than the thickness of the frame member.

[17] The kit according to [16], further including a gel for forming the gel.

According to the presently disclosed subject matter, a device capable of simply measuring the tension of a sheet-like tissue containing cardiomyocytes, which was difficult to handle because of its thinness, is provided. Further, the device can be easily incorporated into a system for measuring the tension of a sheet-like tissue containing cardiomyocytes, and enables acquisition of data reproducibly and stably.

BRIEF DESCRIPTION OF THE DRAWINGS

FIGS. 1A to 1H are views illustrating a tension measuring device, a substrate, and a gel forming lid body of an embodiment of the presently disclosed subject matter;
FIG. 1A is a front view of the tension measuring device;
FIG. 1B is a rear view of FIG. 1A;
FIG. 1C is a perspective view of a second gel adapter holder;
FIG. 1D is a plan view of a first gel adapter holder;
FIG. 1E is a plan view of the tension measuring device;
FIG. 1F is a rear view of the tension measuring device in which the second gel adapter holder is slid up;
FIG. 1G is a front view of the substrate;
FIG. 1H is a front view of the gel forming lid body;
FIG. 2A is a view before assembling the respective members in FIG. 1;
FIG. 2B is a view after assembling the respective members in FIG. 1;
FIGS. 3A to 3H are view illustrating a tension measuring device, a substrate, and a gel forming lid body of an embodiment of the presently disclosed subject matter;
FIG. 3A is a front view of the tension measuring device;
FIG. 3B is a rear view of FIG. 3A;
FIG. 3C is a perspective view of FIG. 3A;
FIG. 3D is a perspective view of a second gel adapter holder;
FIG. 3E is a plan view of a first gel adapter holder;
FIG. 3F is a plan view of the tension measuring device;
FIG. 3G is a front view of the substrate;
FIG. 3H is a front view of the gel forming lid body;
FIGS. 4A and 4B are views of an assembly of the respective members in FIGS. 3A to 3H;
FIG. 4A illustrates a view after assembling the respective members in FIGS. 3A to 3H except for the gel forming lid body;
FIG. 4B illustrates a view after assembling the gel forming lid body with the assembly in FIG. 4A;
FIG. 5A is a perspective view of a first gel adapter holder;
FIG. 5B is a perspective view of a second gel adapter holder;
FIG. 5C is a perspective view of the substrate;
FIG. 5D is a perspective view of the gel forming lid body;

FIG. 6A illustrates a view after assembling the respective members in FIGS. 5A to 5D except for the gel forming lid body;

FIG. 6B illustrates a view after assembling the gel forming lid body with the assembly in FIG. 6A.

FIGS. 7A to 7D are steps of forming a tension measuring device; FIG. 7E is a cross-sectional view of the tension measuring device obtained in FIG. 7D FIGS. 8A and 8B are views showing a step of forming a tension measuring device of an embodiment of the presently disclosed subject matter;

FIG. 9A is a view illustrating a culture medium tank;

FIG. 9B is a view illustrating a culture medium tank mounted with a tension measuring device;

FIG. 9C is a view illustrating the tension measuring device connected to a tension detection unit connector;

FIG. 9D is a view illustrating a part of the tension measuring system;

FIG. 9E is a view illustrating a state where a contracting cardiomyocyte sheet pulls the tension detection unit connector; and FIG. 10 is a view illustrating a tension measuring system of an embodiment of the presently disclosed subject matter.

DETAILED DESCRIPTION OF THE EMBODIMENTS

Figure 2B:
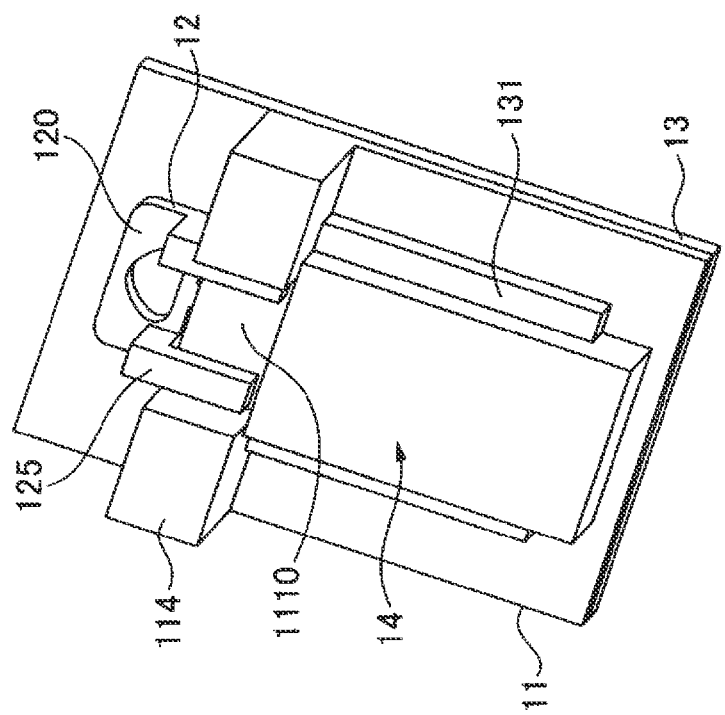
FIGS. 2A and 2B are views of an assembly of the respective members in FIG. 1.

Hereinafter, embodiments of the presently disclosed subject matter will be described with reference to the drawings as needed. The configurations of the embodiments are illustrative and the configuration of the presently disclosed subject matter is not limited to the specific configurations of the embodiments.

<Sheet-Like Tissue Containing Cells>

In this specification, the "sheet-like tissue containing cells" refers to a biological tissue collected from a living body or a thin film-like tissue containing cells. The sheet-like tissue containing cells may be a tissue collected from a living body as it is or a biological tissue obtained by processing a tissue collected from a living body into the form of a sheet. Further, the sheet-like tissue containing cells may be a sheet-like tissue formed by mixing a suspension containing cells with a gel, and may also be a cell sheet. In addition, the sheet-like tissue containing cells may be a tissue formed by directly seeding a cell group on the upper face of a film-like gel, followed by culturing.

In this specification, the "cell sheet" refers to a cell group in the form of a sheet in one layer or a plurality of layers obtained by culturing a cell group containing a plurality of arbitrary cells on a cell culture substrate and exfoliating the cells from the cell culture substrate. As a method for obtaining a cell sheet, for example, a method in which cells are cultured on a stimulus-responsive culture substrate coated with a polymer which changes its molecular structure by a stimulus such as temperature, pH, or light, and the cells are exfoliated in sheets from the stimulus-responsive culture substrate while maintaining the cells in an adhered state by changing the conditions of the stimulus such as temperature, pH, or light so as to change the surface of the stimulus-responsive culture substrate, a method in which cells are cultured on an arbitrary culture substrate and the cultured cells are physically exfoliated using forceps or the like, whereby a cell sheet is obtained, and the like are exemplified. As the stimulus-responsive culture substrate for obtaining a cell sheet, a temperature-responsive culture substrate in which the surface thereof is coated with a polymer which changes its hydration force within a temperature range of 0 to 80° C. is known. On the temperature-responsive culture substrate, cells are cultured in a temperature range in which the hydration force of the polymer is weak, and thereafter, the temperature of the culture solution is changed to a temperature at which the polymer becomes in a state where the hydration force is strong, whereby the cells can be exfoliated as a cell group in the form of a sheet.

The temperature-responsive culture substrate to be used for obtaining a cell sheet is preferably a substrate which changes the hydration force of the surface thereof in a temperature range in which cells can be cultured. The temperature range is preferably a temperature at which cells are generally cultured, for example, from 33° C. to 40° C. A temperature-responsive polymer to be coated on a culture substrate to be used for obtaining a cell sheet may be either a homopolymer or a copolymer. As such a polymer, for example, polymers described in JP-A-2-211865 are exemplified.

A case where poly (N-Isopropylacrylamide) is used as the stimulus-responsive polymer, particularly, as the temperature-responsive polymer will be described as an example (a temperature-responsive culture dish). Poly (N-Isopropylacrylamide) is known as a polymer having a lower critical solution temperature of 31° C., and when it is in a free state, dehydration occurs at a temperature of 31° C. or higher in water to aggregate the polymer chains and cause white turbidity. On the other hand, when the temperature is lower than 31° C., the polymer chains are hydrated and become in a state of being dissolved in water. In the presently disclosed subject matter, this polymer is coated on the surface of a substrate such as a dish and fixed thereto. Therefore, if the temperature is 31° C. or higher, the polymer on the surface of the culture substrate is also dehydrated in the same manner, however, the polymer chains are fixed to the surface of the culture substrate, and therefore, the surface of the culture substrate comes to show hydrophobicity. On the other hand, when the temperature is lower than 31° C., the polymer on the surface of the culture substrate is hydrated, however, the polymer chains are coated on the surface of the culture substrate, and therefore, the surface of the culture substrate comes to show hydrophilicity. The hydrophobic surface at this time is a moderate surface, to which cells are adhered and on which the cells can proliferate, and further, the hydrophilic surface becomes a surface to which cells cannot be adhered. Therefore, when the substrate is cooled to a temperature lower than 31° C., the cells are exfoliated from the surface of the substrate. If the cells are cultured to confluence on the entire culture surface, a cell sheet can be recovered by cooling the substrate to a temperature lower than 31° C. The temperature-responsive culture substrate is not limited as long as it has the same effect, however, for example, UpCell (registered trademark) commercially available from CellSeed, Inc. (Tokyo, Japan), and the like are exemplified.

<Sheet-Like Tissue Containing Cardiomyocytes>

In this specification, the "sheet-like tissue containing cardiomyocytes" refers to a tissue containing at least cardiomyocytes at 10% or more of the number of cells contained in the sheet-like tissue containing cells described above, and the cardiomyocytes are contained therein at, for example, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or 99% or more. The "sheet-like tissue containing cardiomyocytes" to be used in the presently disclosed subject matter is preferably beating cardiomyocytes. The cardiomyocytes which can be used in the presently disclosed subject matter may be any as long as the cells are derived from an animal, and for example, cardiomyocytes of a mammal, a bird, an amphibian, a reptile, or a fish can be used. The cardiomyocytes are preferably derived from a mammal, and for example, cardiomyocytes derived from a mammal such as a mouse, a rat, a human, a monkey, a pig, a dog, a sheep, a cat, a goat, or the like can be used.

The cells which can be used in the presently disclosed subject matter may be primary cells collected from a biological tissue, or may be an established cell line, or may be cells differentiated and induced from pluripotent stem cells or tissue stem cells.

In this specification, the term "pluripotent stem cells" is intended to be a generic name for stem cells having an ability to differentiate into cells of every possible tissue (differentiation pluripotency). The pluripotent stem cells include, although not limited to, embryonic stem cells (ES cells), embryonic carcinoma cells (EC cells), trophoblast stem cells (TS cells), epiblast stem cells (EpiS cells), embryonic germ cells (EG cells), multipotent germline stem cells (mGS cells), induced pluripotent stem cells (iPS cells), Muse cells, and the like. Preferred are ES cells or iPS cells. As the pluripotent stem cells, arbitrary known cells can be used, and for example, pluripotent stem cells described in WO 2009/123349 (PCT/JP2009/057041) can be used.

The cardiomyocytes which can be used in the presently disclosed subject matter may be cells differentiated and induced from pluripotent stem cells. As a method for differentiating pluripotent cells into cardiomyocytes, a known method can be used (see, for example, Matsuura K., et al., Creation of human cardiac cell sheets using pluripotent stem cells, Biochem. Biophys. Res. Commun. 2012, August 24; 425(2): 321-327, or the like).

The sheet-like tissue containing cardiomyocytes may contain cells other than cardiomyocytes. For example, cardiac myoblasts, myoblasts, mesenchymal stem cells, vascular endothelial cells, vascular endothelial progenitor cells, fibroblasts, or the like may be contained.

<Tension Measuring Device (First Embodiment)>

The presently disclosed subject matter provides a device for measuring the tension of a sheet-like tissue containing cardiomyocytes, including:

a first gel adapter holder having a frame member and a first gel holding member provided protruding toward a part of an inside face of the frame member for fixing one end of a film-like gel; and a second gel adapter holder having a second gel holding member for fixing the other end of the gel and a connection member connected to the second gel holding member, wherein the second gel adapter holder is attached to the first gel adapter holder so that the second gel holding member is opposed to the first gel holding member inside the frame member, and the second gel adapter holder has a mechanism for sliding in an axial direction in which the first gel holding member and the second gel holding member are opposed to each other.

FIGS. 1A to 1H show a tension measuring device 1 of an embodiment of the presently disclosed subject matter, and a substrate 13 and a gel forming lid body 14 which are used together with the tension measuring device 1. The tension measuring device 1 can include a first gel adapter holder 11 and a second gel adapter holder 12. The first gel adapter holder 11 can include a frame member 110, which is pierced in a rectangular form inside as shown in FIGS. IA and 1B, and a first gel holding member 111, which is provided protruding toward a part of an inside face (a frame inside bottom face 119 in FIGS. 1A to 1H) of the frame member 110 for fixing one end of a film-like gel G (described later). On both sides of the first gel holding member 111, a space is provided between the first gel holding member 111 and a frame inside side face 118, and in this space, a gel molding protruding member 131 of the substrate 13 described later is fitted. The frame member 110 plays a role in becoming a part of a mold frame when the gel G is formed, and also plays a role in preventing an arbitrary object from coming into contact with the gel G and a sheet-like tissue ST from the lateral side. Further, the tension measuring device 1 can be easily attached to a culture medium tank lid body 21 of a culture medium tank 2 (described later) while maintaining the shape of the gel G and the sheet-like tissue ST by the existence of the frame member 110.

The first gel holding member 111 is provided in parallel with the thin film of the gel G to be fowled. The first gel holding member 111 is provided with one or more first gel holding openings 112. On both ends of the first gel holding member 111, a first gel holding recessed member 113 is further provided.

By changing the thickness of the frame member 110, the thickness of the gel G can be changed as appropriate. The thickness of the frame member 110 is not limited, and may be any thickness as long as the sheet-like tissue containing cardiomyocytes can be adhered thereto and stably held thereon and the gel G does not impede the action of beating and contraction of the sheet-like tissue containing cardiomyocytes, and is a thickness of, for example, from 0.5 mm to 3.0 mm, from 0.5 mm to 2.5 mm, from 0.5 mm to 2.0 mm, from 0.5 mm to 1.5 mm, from 1.0 mm to 3.0 mm, from 1.0 mm to 2.5 mm, from 1.0 mm to 2.0 mm, or from 1.0 mm to 1.5 mm, preferably from 0.5 mm to 2.5 mm, more preferably from 0.5 mm to 1.5 mm The thickness of the first gel holding member 111 is formed thinner than the thickness of the frame member 110. Further, the first gel holding member 111 is provided at an intermediate position in the thickness direction of the frame member 110 on the frame inside bottom face 119. Thereby, the gel G covers both the upper face and the bottom face of the first gel holding member 111, and thus the gel G is reliably held.

The second gel adapter holder 12 has a second gel holding member 121 for fixing the other end of the gel G and a connection member 120 connected to the second gel holding member 121. As shown in FIG. 1C, the connection member 120 and the second gel holding member 121 are connected to each other through a T-shaped member 124. The second gel holding member 121 is provided in parallel with the gel G to be formed. The second gel holding member 121 is provided with one or more second gel holding openings 122. On both ends of the second gel holding member 121, a second gel holding recessed member 123 is further provided. The thickness of the second gel holding member 121 is formed thinner than the thickness of the T-shaped member 124, and preferably, the second gel holding member 121 has the same thickness as the first gel holding member 111.

Further, the second gel holding member 121 is provided at an intermediate position in the thickness direction of the T-shaped member 124. Thereby, the gel G covers both the upper face and the bottom face of the second gel holding member 121, and thus the gel G is reliably held.

The connection member 120 is provided with a connection opening 126 for connecting a tension detection unit connector 3. Further, the connection member 120 is provided with one or more (in this embodiment, two) L-shaped members 125 for detachably attaching the second gel adapter holder 12 to the first gel adapter holder 11. The L-shaped member 125 is fitted in a first guide groove 1110 provided in a part of a frame upper member 114 of the first gel adapter holder 11. Further, in an upper part of the rear face of the frame member 110, a second guide groove 1111 for fitting a part of the T-shaped member 124 of the second gel adapter holder 12 therein is provided. The width of the second guide groove 1111 is designed so that a part of the T-shaped member 124 is fitted therein and the second gel adapter holder 12 is not precluded from sliding in the axial direction in which the first gel holding member and the second gel holding member are opposed to each other. Further, the depth of the second guide groove 1111 may be substantially the same as the thickness of the T-shaped member 124. Thereby, in the case where a part of the T-shaped member 124 is fitted in the second guide groove 1111, the rear face of the second gel adapter holder 12 and the rear face of the first gel adapter holder 11 are positioned on substantially the same plane (see FIG. 1E). A frame upper part rear face 1112 of the first gel adapter holder 11 is recessed by one step from the frame member 110 and shares a plane with the second guide groove 1111. According to this, the second gel adapter holder 12 can slide up and down without the I-shaped member 124 being caught by the frame member 110 (see FIG. 1F). In this embodiment, in the case where the second gel adapter holder 12 slides up, the upper part (a stopper 115) of the frame member 110 comes into contact with the T-shaped member 124, and restricts the slidable range of the second gel adapter holder 12. Therefore, damage to the gel G and the sheet-like tissue ST containing cardiomyocytes is prevented.

A gel poured into the first gel holding opening 112 and the second gel holding opening 122 plays a role in fixing one end of the film-like gel G to the first gel holding member 111 and the other end of the gel G to the second gel holding member 121 after it is solidified. The first gel holding recessed member 113 and the second gel holding recessed member 123 also achieves an effect of fixing the gel G after the gel is solidified. The number, shape, and size of first gel holding openings 112 and second gel holding openings 122 are determined as appropriate according to the size of the gel G to be formed, the viscosity, strength, and polymerization degree of the gel, and the like. For example, 1 to 10, 1 to 5, 2 to 5, or 2 to 4 first gel holding openings 112 and second gel holding openings 122 may be provided. The shape of the first gel holding member 111 and the second gel holding member 121 is preferably symmetric.

In order to form the gel G in the tension measuring device 1, the substrate 13 and the gel forming lid body 14 shown in FIGS. 1G to 1H are used. On a plane member 130 of the substrate 13, a pair of gel molding protruding members 131 to be fitted between the first gel holding member 111 and the second gel holding member 121, and the frame inside side face 118 are provided. Further, on the substrate 13, a gel forming protruding member upper part 132 to be fitted in the frame upper part rear face 1112 of the frame member 110 is provided. Moreover, on the substrate 13, an L-shaped part fitting groove 133 is provided between a pair of gel forming protruding member upper parts 132. In the L-shaped part fitting groove 133, the T-shaped member 124 of the second gel adapter holder 12 is fitted.

The width of the gel forming lid body 14 substantially coincides with the width of the inner face of the pair of gel molding protruding members 131 provided on the substrate 13. According to this, the gel forming lid body 14 is fitted between the pair of gel molding protruding members 131. The length of the gel forming lid body 14 of this embodiment may be any length as long as the gel forming lid body 14 covers the space where the gel G is formed.

Figure 2A:
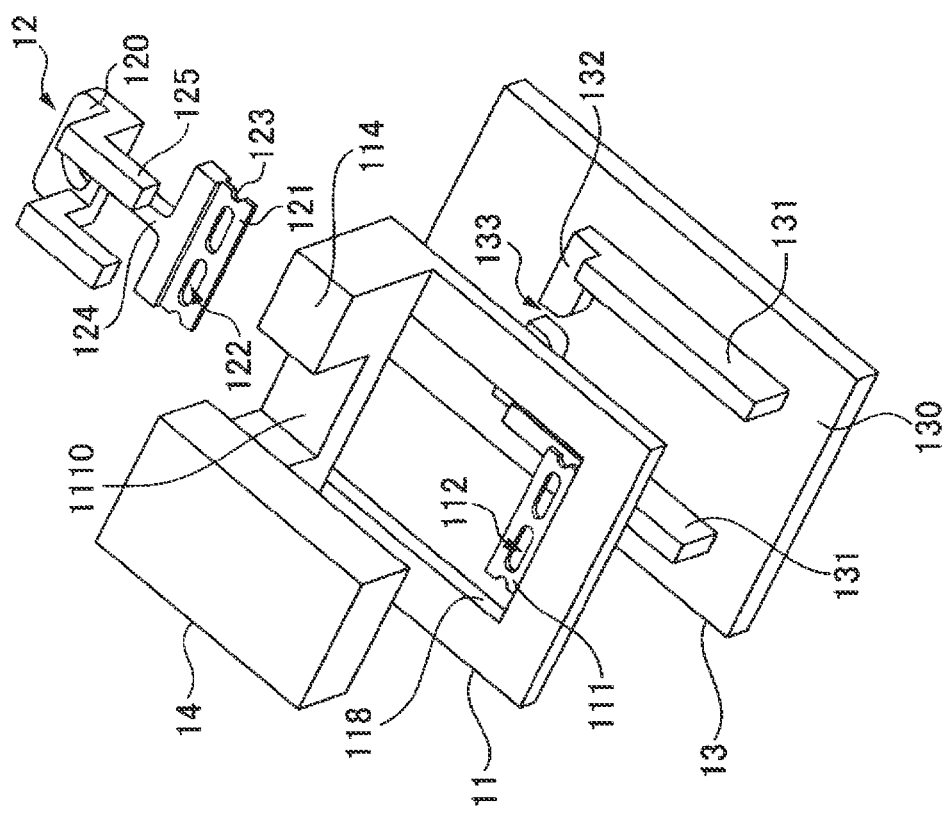

FIG. 2A shows a view before assembling the first gel adapter holder 11, the second gel adapter holder 12, the substrate 13, and the gel forming lid body 14, and FIG. 2B shows a view after assembling these members.

<Tension Measuring Device (Second Embodiment)>

FIGS. 3A to 4B are views showing a tension measuring device 1a (a first gel adapter holder 11a and a second gel adapter holder 12a), a substrate 13a, and a gel forming lid body 14a in another embodiment. The basic configuration and the concept of the invention are the same as the tension measuring device 1 (the first gel adapter holder 11 and the second gel adapter holder 12), the substrate 13, and the gel forming lid body 14, and the respective members provided therein of the first embodiment. The above-mentioned explanation for the respective corresponding members of the first embodiment is applied to the explanation for the tension measuring device 1a (the first gel adapter holder 11a and the second gel adapter holder 12a), the substrate 13a, and the gel forming lid body 14a, and the respective members provided therein given the same reference numerals as the tension measuring device 1 (the first gel adapter holder 11 and the second gel adapter holder 12), the substrate 13, and the gel forming lid body 14, and the respective members provided therein of the first embodiment except that "a" is added to the reference numeral of each member. Here, only members to which the explanation of the respective members of the first embodiment is not applied will be described.

In the second gel adapter holder 12a, as shown in FIG. 3D, a connection member 120a and a second gel holding member 121a are connected to each other through a second gel adapter holder main body 127a. The second gel adapter holder main body 127a is provided with a stopper opening 128a.

In an upper part of the rear face of a frame member 110a, a second guide groove 1111a for fitting the second gel adapter holder main body 127a therein is provided. The second guide groove 1111a is further provided with a stopper 115a (see FIG. 3E). In the case where the second gel adapter holder 12a is attached to the first gel adapter holder 11a, the stopper 115a comes into contact with the upper side or the lower side of the stopper opening 128a, and therefore, the width at which the second gel adapter holder 12a slides up and down can be restricted. Thereby, damage to a gel G and a sheet-like tissue ST containing cardiomyocytes is prevented.

On a plane member 130a of the substrate 13a, a pair of gel molding protruding members 131a to be fitted between a first gel holding member 111a and a second gel holding member 121a, and a frame inside side face 118a are provided. The width of the gel molding protruding member 131a is designed so as to fill a space to be formed between the first gel holding member 111a and the second gel holding member 121a, and the frame inside side face 118a. The height of the gel molding protruding member 131a is designed to be the same as the thickness of the frame member 110a. Further, the length of the gel molding protruding member 131a is designed to be the same as that of the frame inside side face 118a. In an upper part of the substrate 13a, a protruding member to become a substrate upper member 134a is provided. By the substrate upper member 134a, the second gel adapter holder 12a can be prevented from sliding up when the gel G is formed.

The first gel adapter holder 11a in this embodiment can include a surrounding member 116a vertically provided on the outer periphery of the frame member 110a. The gel forming lid body 14a is designed so as to be fitted in the surrounding member 116a (see FIG. 3H). The gel forming lid body 14a is provided with a grip member 140a so as to facilitate the detachment of the gel forming lid body 14a from the surface of the gel G closely adhered thereto after the gel G is formed.

FIG. 4A shows a state where the first gel adapter holder 11a, the second gel adapter holder 12a, and the substrate 13a are assembled, and FIG. 4B shows a state where the gel forming lid body 14a is further assembled with the assembly in FIG. 4A.

<Tension Measuring Device (Third Embodiment)>

Figure 5B:
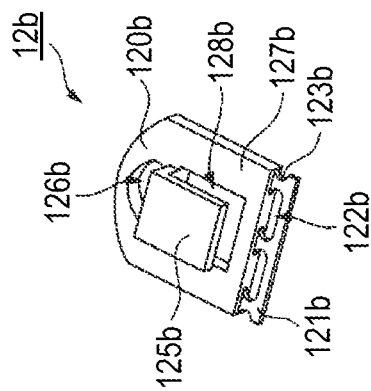
FIGS. 5A to 5D are views illustrating a tension measuring device, a substrate, and a gel forming lid body of an embodiment of the presently disclosed subject matter.
Figure 5D:
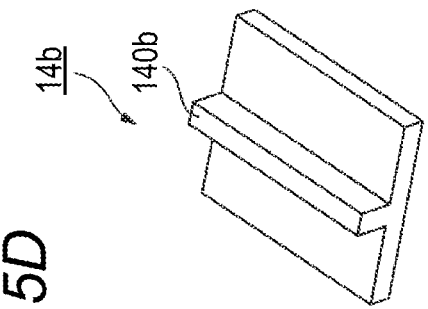
Figure 5A:
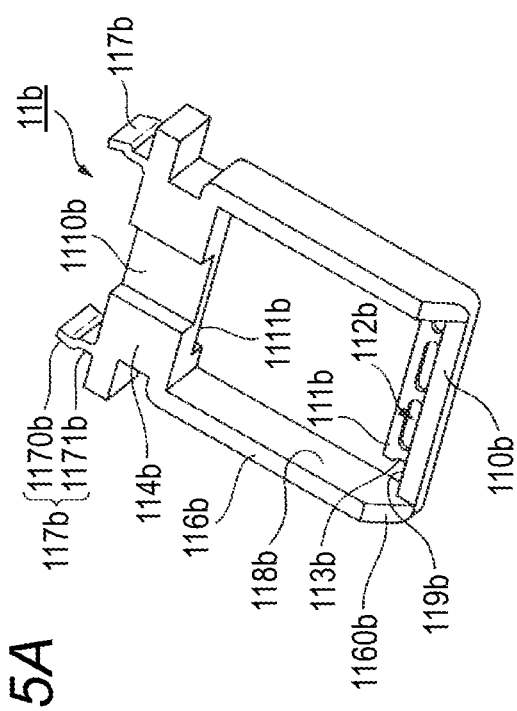
Figure 5C:
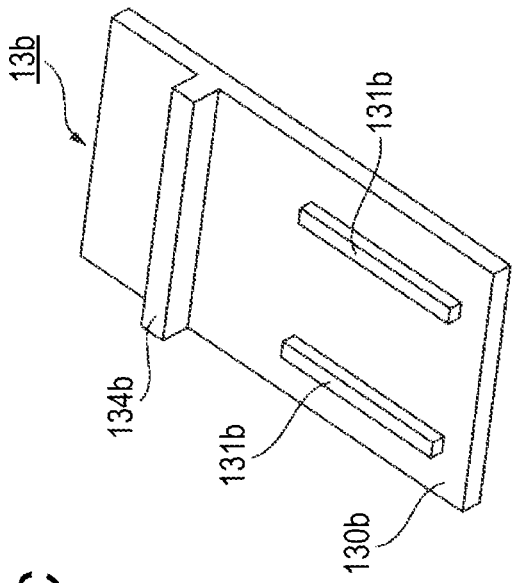
Figure 6A:
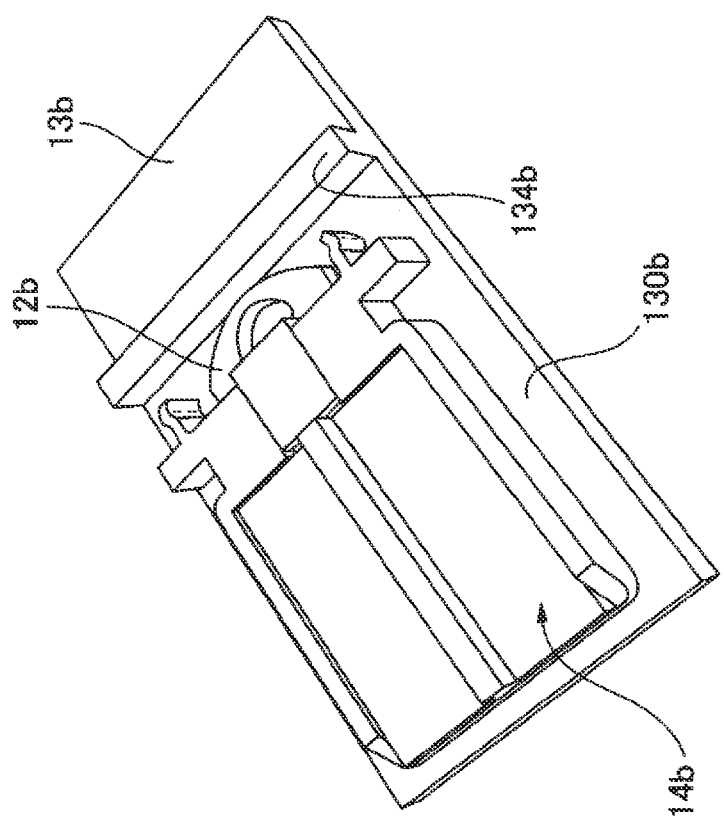
FIGS. 6A and 6B are views of an assembly of the respective members in FIGS. 5A to 5D.
Figure 6B:
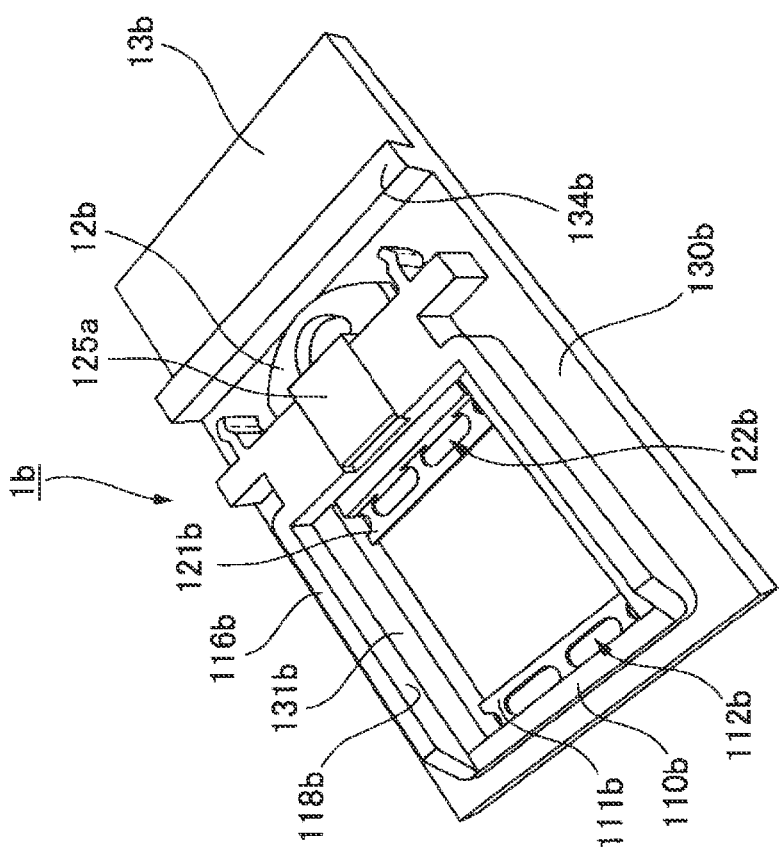

FIGS. 5A and 6B are views showing a tension measuring device 1b (a first gel adapter holder 11b and a second gel adapter holder 12b), a substrate 13b, and a gel forming lid body 14b in another embodiment. The basic configuration and the concept of the invention are the same as the tension measuring device (1, 1a) (the first gel adapter holder (11, 11a) and the second gel adapter holder (12, 12a)), the substrate (13, 13a), and the gel forming lid body (14, 14a), and the respective members provided therein of the first embodiment and the second embodiment. The above-mentioned explanation for the respective corresponding members of the first embodiment or the second embodiment is applied to the explanation for the tension measuring device 1b (the first gel adapter holder 11b and the second gel adapter holder 12b), the substrate 13b, and the gel forming lid body 14b, and the respective members provided therein given the same reference numerals as the tension measuring device (1, 1a) (the first gel adapter holder (11, 11a) and the second gel adapter holder (12, 12a)), the substrate (13, 13a), and the gel forming lid body (14, 14a), and the respective members provided therein of the first embodiment or the second embodiment except that "b" is added to the reference numeral of each member. Here, only members to which the explanation of the respective members of the first embodiment or the second embodiment is not applied will be described.

A first gel holding opening 112b of the first gel adapter holder 11b is formed integrally with a frame inside bottom face 119b as shown in FIG. 5A. Further, a frame member 110b is formed integrally with a surrounding member 116b as shown in FIG. 5A. In a frame upper member 114b of the first gel adapter holder 11b, a pair of protruding members for attachment and detachment 117b for attaching and detaching the tension measuring device 1b is provided at a device installation opening 24 of a culture medium tank lid body 21 described later. The protruding member for attachment and detachment 117b is formed from a protruding member upper part 1170b and a protruding member lower part 1171b. The protruding member upper part 1170b is provided obliquely inward so as to be inserted into the device installation opening 24. Further, the pair of protruding members for attachment and detachment 117b are bilaterally symmetrically provided in the frame upper member 114b. The pair of protruding members for attachment and detachment 117b are provided at an interval so that they can be attached to and detached from the device installation opening 24. The pair of protruding members for attachment and detachment 117b are inserted into the device installation opening 24 by being deformed inward due to its elasticity and fixed to the device installation opening 24 by being restored to the original shape due to the restoring force of the pair of protruding members for attachment and detachment 117b.

As shown in FIG. 5B, a second gel holding opening 122b of the second gel adapter holder 12b is formed integrally with a second gel adapter holder main body 127b.

FIG. 6A shows a state where the first gel adapter holder 11b, the second gel adapter holder 12b, and the substrate 13b are assembled. FIG. 6B shows a state where the gel forming lid body 14b is further assembled with the assembly in FIG. 6A.

As a material of the tension measuring device (1, 1a, 1b) (the first gel adapter holder (11, 11a, 11b) and the second gel adapter holder (12, 12a, 12b)), the substrate (13, 13a, 13b), and the gel forming lid body (14, 14a, 14b), for example, polyethylene, polypropylene, polycarbonate, polystyrene, polyvinyl chloride, nylon, polyurethane, polyurea, polylactic acid, polyglycolic acid, polyvinyl alcohol, polyvinyl acetate, poly(meth)acrylate, a poly(meth)acrylate derivative, polyacrylonitrile, poly(meth)acrylamide, a poly(meth)acrylamide derivative, polysulfone, polycarbonate, cellulose, a cellulose derivative, polysilicone, a glass, a ceramic, a metal, and the like are exemplified.

<Kit for Forming Device for Measuring Tension of Sheet-Like Tissue Containing Cardiomyocytes>

The presently disclosed subject matter provides a kit for forming a device for measuring the tension of a sheet-like tissue containing cardiomyocytes, including:

a first gel adapter holder having a frame member and a first gel holding member provided protruding toward a part of an inside face of the frame member for fixing one end of a film-like gel;

a second gel adapter holder having a second gel holding member for fixing the other end of the gel and a connection member connected to or integrated with the second gel holding member;

a substrate having a pair of gel molding protruding members fitted along the inside face of the frame member; and a gel forming lid body having a face parallel to a gel contact face of the substrate for forming the upper face of the gel, wherein the second gel adapter holder is attached to the first gel adapter holder so that the second gel holding member is opposed to the first gel holding member inside the frame member, and the second gel adapter holder has a mechanism for sliding in an axial direction in which the first gel holding member and the second gel holding member are opposed to each other.

Further, the kit may be a kit including a gel for forming the film-like gel between the first gel holding member and the second gel holding member.

In the presently disclosed subject matter, as the gel to be used for forming the film-like gel, any gel can be utilized as long as (1) the sheet-like tissue containing cardiomyocytes can adhere to the gel, (2) the gel has a strength capable of maintaining the form of a sheet, and (3) the gel does not adversely affect the growth of cells, the functional expression thereof, etc., that is, it is a biocompatible gel. The gel which can be used in the presently disclosed subject matter is, for example, a hydrogel. As the hydrogel which can be used in the presently disclosed subject matter, for example, a hydrogel in which a water-soluble, hydrophilic, or water-absorbing synthetic polymer such as polyacrylamide, polyacrylic acid, polyhydroxyethylmethacrylate, polyvinyl alcohol, polylactic acid, or polyglycolic acid, a polysaccharide, a protein, a nucleic acid, or the like is chemically crosslinked is exemplified. Examples of the polysaccharide include glycosaminoglycans such as hyaluronic acid and chondroitin sulfate, starch, glycogen, agarose, pectin, cellulose, and the like. Further, examples of the protein include collagen, gelatin which is a hydrolysate thereof, proteoglycan, fibronectin, vitronectin, laminin, entactin, tenascin, thrombospondin, von Willebrand factor, osteopontin, fibrinogen (for example, a fibrin gel obtained by reacting fibrinogen with thrombin), and the like. These hydrogels may be used after being subjected to a crosslinking treatment using a known method to increase the strength thereof. The gel to be used in the presently disclosed subject matter is preferably a fibrin gel. In one embodiment of the presently disclosed subject matter, the film-like gel may be a gel formed by mixing cells in advance.

<Method of Using Kit for Forming Device for Measuring Tension of Sheet-Like Tissue Containing Cardiomyocytes>

A method of using the kit for forming a device for measuring the tension of a sheet-like tissue containing cardiomyocytes will be described with reference to FIGS. 7A to 8B.

Figure 7A:
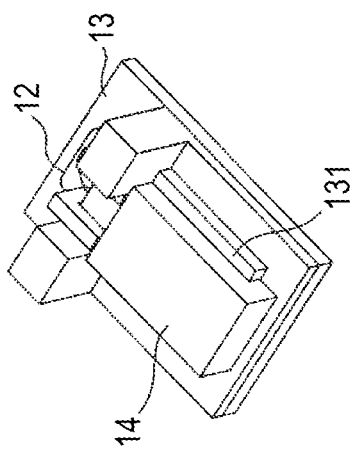
FIGS. 7A to 7E are views showing a step of forming a tension measuring device using a kit for forming a tension measuring device of an embodiment of the presently disclosed subject matter.

(i) The substrate 13 is mounted on the tension measuring device 1 (the first gel adapter holder 11 and the second gel adapter holder 12), and a gel (for example, a mixed liquid of fibrinogen (Type I-S derived from bovine plasma, SIGMA), thrombin (T4648 derived from bovine plasma, SIGMA), a $CaCl_2$ solution (8 mM), and Factor XIII (Fibrogammin P for intravenous injection, CSL Behring) before curing is injected into a film-like gel forming member S using a pipette P (FIG. 7A). At this time, the gel before curing is injected while being careful so as to prevent air from mixing in the first gel holding opening 112 and the second gel holding opening 122.

Figure 7B:
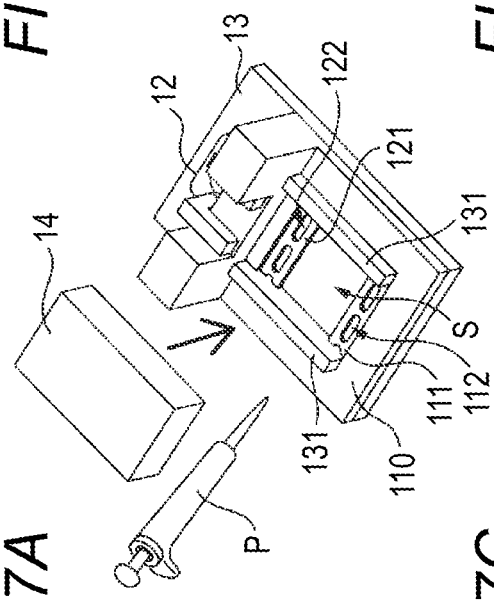

(ii) After injection, the film-like gel forming member S is covered with the gel forming lid body 14 (FIG. 7B).

Figure 7C:
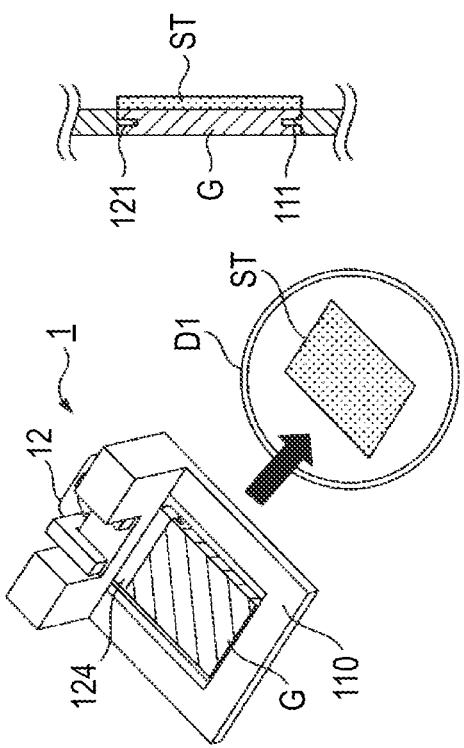

(iii) After the gel is cured, the gel forming lid body 14 and the substrate 13 are detached from the tension measuring device I (FIG. 7C).

(iv) Apart from the above, a cell group containing cardiomyocytes is seeded on a temperature responsive culture dish D1 (for example, UpCell (registered trademark), CellSeed, Inc. Tokyo, Japan) and previously cultured at 37° C. until confluence is reached.

Figure 7D:
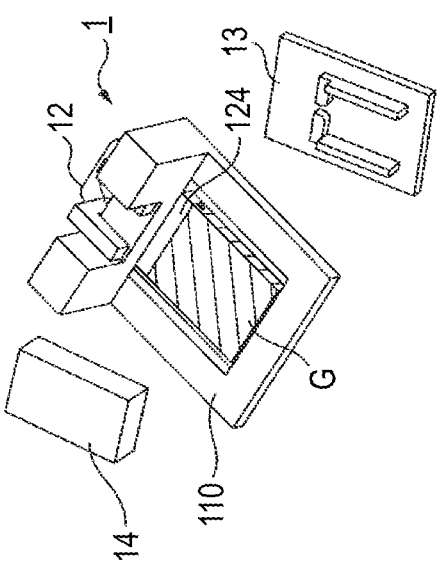

(v) On the sheet-like tissue ST containing cardiomyocytes in the temperature responsive culture dish D1, the tension measuring device 1 including the film-like gel obtained above is placed (FIG. 7D).

Figure 7E:
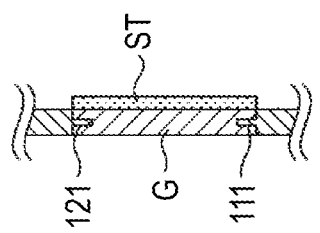
Figure 8A:
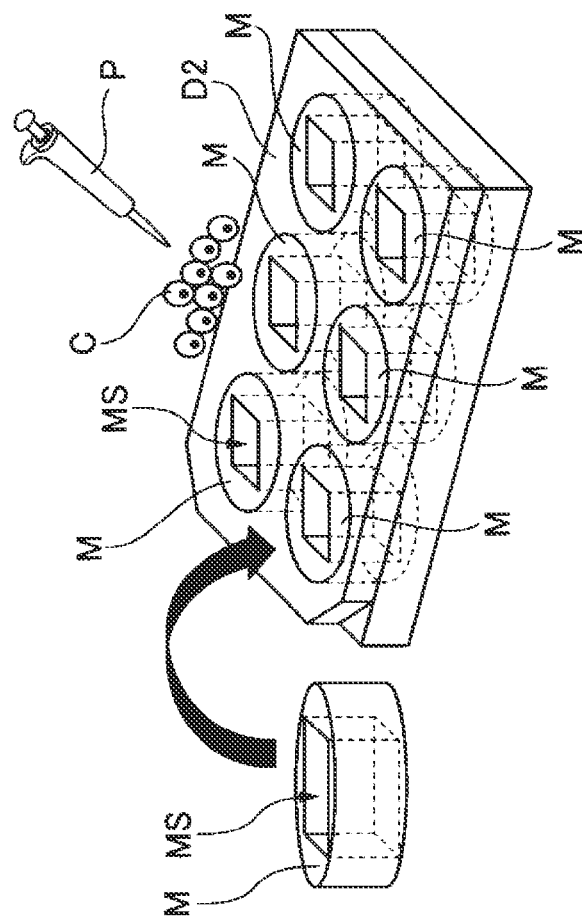
Figure 8B:
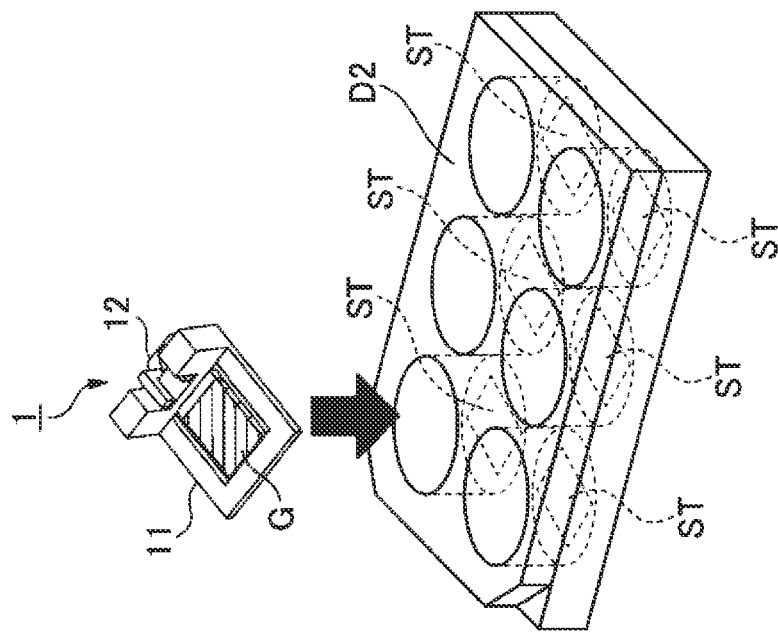

(vi) Thereafter, the sheet-like tissue ST containing cardiomyocytes is exfoliated from the temperature responsive culture dish D1 while being maintained at a temperature equal to or lower than the lower critical solution temperature of the temperature responsive culture dish D1, for example, 20° C., and at the same time, the sheet-like tissue ST containing cardiomyocytes is adhered to the lower face of the gel G (FIG. 7E).

The sheet-like tissue ST containing cardiomyocytes in a single layer may be adhered to the gel G or in a plurality of layers may be adhered thereto. In order to adhere the sheet-like tissue ST containing cardiomyocytes in a plurality of layers, by repeating the above-mentioned (v) and (vi) arbitrary times, a desired material is obtained.

It is preferred that the sheet-like tissue ST containing cardiomyocytes is formed into the same shape as that of the gel G in advance before it is adhered to the gel G. As a method for molding the sheet-like tissue ST into the same shape as that of the gel G, for example, a method in which the cultured sheet-like cell group is cut using a surgical knife or the like, and a method in which cells are seeded by utilizing a mold M which limits the region where the cells are adhered to the shape of the gel G in advance are exemplified (see, for example, FIG. 8A). By adhering the lower face of the gel G onto the sheet-like tissue ST containing cardiomyocytes formed into the shape of the gel G, the sheet-like tissue ST containing cardiomyocytes can be simply adhered to the gel G without contraction of the sheet-like tissue ST containing cardiomyocytes (see FIG. 8B).

In another embodiment, the sheet-like tissue ST containing cardiomyocytes may be formed by directly seeding the cell group containing cardiomyocytes on the upper face of the film-like gel G fowled in the above-mentioned step (iii), followed by culturing the cells at 37° C. until confluence or subconfluence is reached. By doing this, the film-like gel G to which the sheet-like tissue ST containing cardiomyocytes is adhered can be obtained.

The tension measuring device 1 of the presently disclosed subject matter may be provided as a device in which the film-like gel G is formed in advance between the first gel holding member 111 and the second gel holding member 121 by the above-mentioned using method, and also may be provided as a device in which the sheet-like tissue ST containing cardiomyocytes is further adhered to the film-like gel G.

<System for Measuring Tension of Sheet-Like Tissue Containing Cardiomyocytes>

The presently disclosed subject matter also provides a system for measuring the tension of a sheet-like tissue containing cardiomyocytes. The system for measuring the tension of a sheet-like tissue containing cardiomyocytes includes, for example, the following members:

(1) a device which is a device for measuring the tension of a sheet-like tissue including:

a first gel adapter holder having a frame member and a first gel holding member provided protruding toward a part of an inside face of the frame member for fixing one end of a film-like gel; and a second gel adapter holder having a second gel holding member for fixing the other end of the gel and a connection member connected to the second gel holding member, wherein the second gel adapter holder is attached to the first gel adapter holder so that the second gel holding member is opposed to the first gel holding member inside the frame member, the second gel adapter holder has a mechanism for sliding in an axial direction in which the first gel holding member and the second gel holding member are opposed to each other, a film-like gel is provided between the first gel holding member and the second gel holding member, and a sheet-like tissue containing cardiomyocytes adhered to the lower face of the film-like gel is included;

(2) a culture medium tank for dipping the device (1);

(3) a tension detection unit which is connected to the connection member of the second gel adapter holder;

(4) an arithmetic unit which is connected to the tension detection unit, arithmetically processes a signal detected by the tension detection unit, and calculates the tension; and (5) an output unit which displays the result calculated by the arithmetic unit.

Figure 9A:
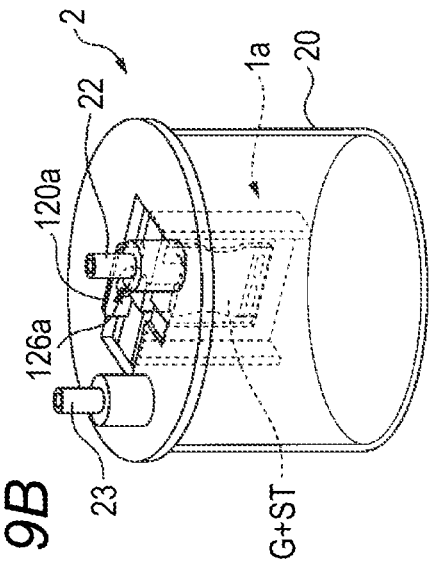
FIGS. 9A to 9E are views illustrating a tension measuring system of an embodiment of the presently disclosed subject matter.
Figure 9B:
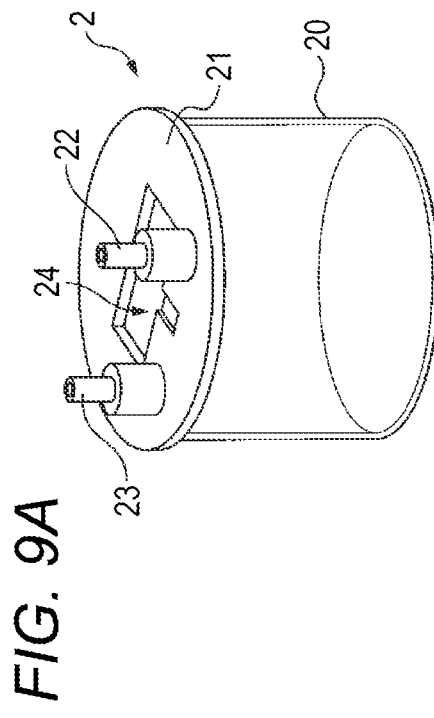
Figure 9D:
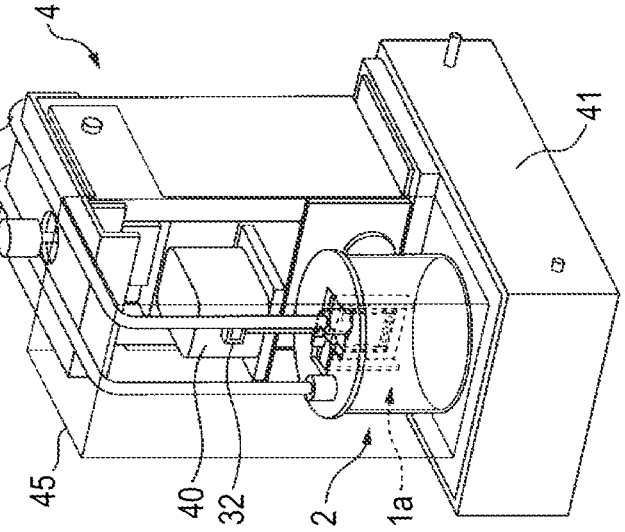
Figure 9C:
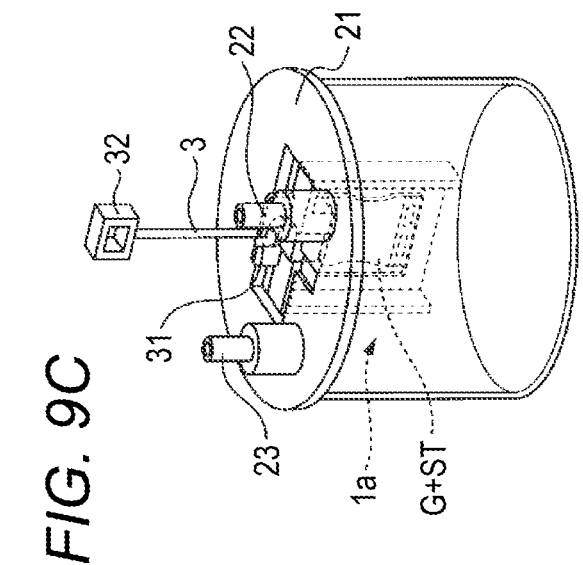

The tension measuring device including a film-like gel and a sheet-like tissue containing cardiomyocytes adhered to the film-like gel is dipped in a culture medium tank 2. The culture medium tank 2 is composed of a culture medium tank main body 20 and a culture medium tank lid body 21. The culture medium tank lid body 21 includes a culture medium supply line connector 22 and a culture medium discharge line connector 23, which are connected to a culture medium supply line 42 and a culture medium discharge line 43, respectively. According to this, a culture medium in the culture medium tank 2 can be replaced. The culture medium tank lid body 21 is provided with a device installation opening 24. As shown in FIG. 9B, a tension measuring device (1, 1*a*, 1*b*) including a gel G and a sheet-like tissue ST containing cardiomyocytes is fitted in the device installation opening 24. A frame member (110, 110*a*) of the tension measuring device (1, 1*a*, 1*b*) may be provided with a protruding member so that the tension measuring device (1, 1*a*, 1*b*) does not fall from the device installation opening 24. For example, as described above, it may be fixed by the protruding member for attachment and detachment 117*b*.

Figure 9E:
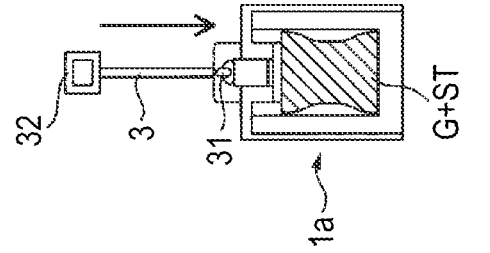

A hook 31 of a tension detection unit connector 3 is passed through a connection opening (126, 126*a*) of a second gel adapter holder (12, 12*a*, 12*b*), whereby the culture medium tank 2 is installed on a culture system 4. The culture system is provided with a tension detection unit 40. A tension detection unit connection member 32 of the tension detection unit connector 3 is connected to the tension detection unit 40. When the sheet-like tissue ST containing cardiomyocytes contracts, the second gel adapter holder (12, 12*a*, 12*b*) is pulled downward, and a load is detected by the tension detection unit 40 through the tension detection unit connector 3 (FIG. 9E). As the tension detection unit 40, for example, a known load cell can be used. According to this, a contraction force (tension) generated by the beating of the sheet-like tissue ST containing cardiomyocytes can be measured. The tension detection unit connector 3 may be any as long as it has a function to connect the second gel adapter holder (12, 12*a*, 12*b*) to the tension detection unit 40, and may be a sandwiching unit (not shown) other than the hook 31.

The culture medium tank lid body 21 may be further provided with a reagent supply opening although not shown in the drawing. By adding an arbitrary drug through the reagent supply opening, the effect of the drug on the cardiomyocytes can be examined. The drug may be supplied into the culture medium tank 2 by adding the drug to a culture medium reservoir tank (not shown) connected to the culture medium supply line 42. Although not shown in the drawing here, the culture medium is supplied to the culture medium tank 2 by, for example, a tube pump, and the culture medium is discharged by the same tube pump. The culture medium tank 2 may be further provided with a known pH sensor, a known dissolved oxygen sensor, a known temperature sensor, or the like.

A culture control member 41 of the culture system 4 includes a heater so as to keep the temperature of the culture medium constant. Further, it may have a magnetic stirrer function. According to this, the culture medium in the culture medium tank 2 can be stirred. The culture system 4 is provided with a hood 44 so as to prevent a foreign substance from mixing into the culture medium tank 2.

FIG.10 shows a tension measuring system 5 of an embodiment of the presently disclosed subject matter. The tension detection unit 40 of the culture system 4 mounted with the tension measuring device (1, 1*a*, 1*b*) is electrically connected to an arithmetic unit 51 through a cable 52. A signal detected by the tension detection unit 40 is input to the arithmetic unit 51 through the cable 52, and the signal is arithmetically processed by the arithmetic unit 51, whereby the tension is calculated. The calculated result is displayed on an output unit, for example, a monitor or the like, electrically connected to the arithmetic unit 51.

What is claimed is:

1. A device for measuring a tension of tissue containing cardiomyocytes comprising: a first gel adapter holder having a frame member and a first gel holding member protruding toward a part of an inside face of the frame member so as to fix one end of a film of gel; and a second gel adapter holder having a second gel holding member for fixing the other end of the gel and a connection member connected to the second gel holding member, wherein the second gel adapter holder is attached to the first gel adapter holder so that the second gel holding member is opposed to the first gel holding member inside the frame member, and the second gel adapter holder has a mechanism for sliding in an axial direction in which the first gel holding member and the second gel holding member are opposed to each other; wherein the second gel adapter holder is detachably attached to the first gel adapter holder so that the second gel holding member is opposed to the first gel holding member inside the frame member, and wherein the connection member is provided with one or more L-shaped members for detachably attaching the second gel adapter holder to the first gel adapter holder wherein the L-shaped member is fitted in a first guide groove provided in the frame member.

2. The device according to claim 1, wherein the first gel holding member has one or more first gel holding openings and the second gel holding member has one or more second gel holding openings.

3. The device according to claim 2, wherein two to five first gel holding openings and two to five second gel holding openings are provided.

4. The device according to claim 1, wherein the thicknesses of the first gel holding member and the second gel holding member are thinner than the thickness of the frame member.

5. The device according to claim 1, wherein the thickness of the frame member is from 0.5 mm to 3.0 mm.

6. The device according to claim 1, wherein the first gel adapter holder is provided with a stopper for restricting the slidable range of the second gel adapter holder.

7. The device according to claim 1, wherein the film of gel is provided between the first gel holding member and the second gel holding member.

8. The device according to claim 7, wherein the gel is a hydrogel.

9. The device according to claim 7, wherein the gel is a fibrin gel.

10. The device according to claim 7, wherein the tissue containing cardiomyocytes is adhered to the film of gel.

11. The device according to claim 10, wherein the tissue is a cell sheet.

12. A system for measuring a tension of tissue containing cardiomyocytes comprising:
the device according to claim 10;
a culture medium tank into which the device is to be dipped;
a tension detection unit which is connected to the connection member of the second gel adapter holder;

an arithmetic unit which is connected to the tension detection unit, arithmetically processes a signal detected by the tension detection unit, and calculates the tension; and an output unit which displays the result calculated by the arithmetic unit.

13. The system according to claim 12, wherein the tension detection unit is a load cell.

* * * * *